United States Patent [19]

Boeck et al.

[11] Patent Number: 4,717,714

[45] Date of Patent: Jan. 5, 1988

[54] A-51568B ANTIBIOTIC

[75] Inventors: LaVerne D. Boeck; Gary G. Marconi; Marvin M. Hoehn, all of Indianapolis, Ind.

[73] Assignee: Eli Lilly and Company, Indianapolis, Ind.

[21] Appl. No.: 775,071

[22] Filed: Sep. 12, 1986

Related U.S. Application Data

[62] Division of Ser. No. 561,008, Dec. 13, 1983, Pat. No. 4,558,008.

[51] Int. Cl.[4] .................... A61K 37/02; A61K 31/71; C07H 15/20
[52] U.S. Cl. ..................................... 514/10; 530/317; 514/25; 536/16.8; 536/18.1
[58] Field of Search ................ 260/112.5 R; 536/18.1, 536/16.8; 514/25, 10; 530/117

[56] References Cited

U.S. PATENT DOCUMENTS 4,547,488  10/1985  Merkel ................................ 536/18.1
4,552,701  11/1985  Nagarajan et al. ................. 536/18.1

Primary Examiner—J. R. Brown
Assistant Examiner—Elli Peselev
Attorney, Agent, or Firm—Robert A. Conrad; Leroy Whitaker

[57] ABSTRACT

The novel glycopeptide antibiotic A-51568B is produced by submerged, aerobic fermentation of *Nocardia orientalis* NRRL 15232. A-51568B demonstrates antibiotic activity against gram-positive bacteria.

4 Claims, No Drawings

A-51568B ANTIBIOTIC

This application is a division of application Ser. No. 561,008, filed 12/13/83, now U.S. Pat. No. 4,558,008.

SUMMARY OF THE INVENTION

This invention relates to A-51568B, a new glycopeptide antibiotic. A-51568B, which will be called Factor B for convenience, has the structure 1:

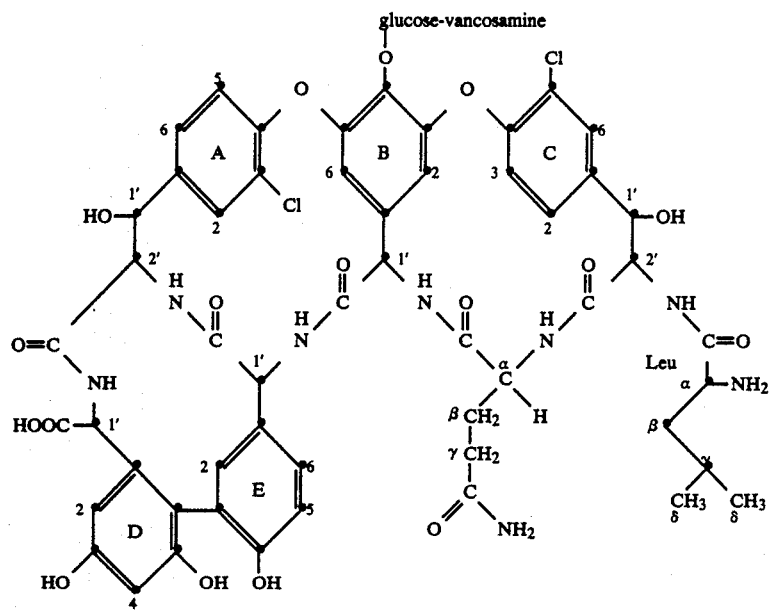

Although no stereochemical assignments are indicated in the structure given herein, the stereochemistry of Factor B is identical to that of Vancomycin B.

Factor B inhibits the growth of pathogenic microorganisms, in particular, those within the grampositive genera Staphylococcus and Streptococcus, which are resistant to penicillin.

This invention further relates to a method of producing Factor B by culturing *Nocardia orientalis* NRRL 15232 under submerged aerobic fermentation conditions until a substantial level of antibiotic is produced.

The microorganism *Nocardia orientalis* NRRL 15232, also referred to herein as the A51568.1 strain, is described in U.S. application Ser. No. 450,880, filed Dec. 20, 1982 by Marvin M. Hoehn and Gary G. Marconi, herein incorporated by reference. NRRL 15232 (A-51568.1) is classified as a strain of *Nocardia orientalis* (Pittenger and Brigham) Pridham & Lyons, ATCC 19795. The A-51568.1 strain of *N. orientalis* has been deposited in the permanent culture collection of the Northern Regional Research Center, U.S. Department of Agriculture Research Service, Peoria, Ill., from which it is available to the public under the accession number NRRL 15232.

Culturing the A-51568.1 strain under submerged aerobic conditions produces a substantial amount of the novel antibiotic A-51568, which is a demethylvancomycin analogue differing from the instant A-51568B and which is further described in the above U.S. application. As will be recognized by those familiar with antibiotic production by fermentation, A-51568 and A-51568B will be produced in varying ratios depending upon the fermentation conditions used. A-51568 is generally produced in a greater amount than A-51568B. Both A-51568 and A-51568B are removed from broth filtrate by adsorbtion onto Diaion HP-20 resin and are eluted with 50% water/methanol after the resin was first washed with water and 25 percent methanol in water. A-51568 and A-51568B are further purified, then separated by column chromatography and high performance liquid chromatography.

DETAILED DESCRIPTION OF THE INVENTION

The following paragraphs describe the properties of Factor B. The structure of Factor B is shown in formula 1.

Factor B is a white, amorphous solid. The antibiotic has a molecular weight of 1447, as determined by fast-atom-bombardment mass spectrometry.

The proton nuclear magnetic resonance spectrum of antibiotic A-51568B was determined in dimethylsulfoxide at 60° C. and 360 MHz. The several six-membered rings of the structural formula are identified by letters of the alphabet, as indicated in the above formula 1. The Table of Chemical Shifts, expressed in parts per million (ppm), follows in Table 1.

TABLE 1

Chemical Shifts for A-51568B (60° C.)

| Assignment | Chem. Shift | Assignment | Chem. Shift |
|---|---|---|---|
| Ring A | | Glutamine | |
| —NH | 6.54 | —NH | 6.83 |
| -2' | 4.19 | -α | 4.06 |
| -1' | 5.13 | -β | 1.67 |
| —OH | 5.85 | γ | 1.87 |
| -2 | 7.84 | —NH$_2$ | 6.83 & |
| -5 | 7.29 | | |
| -6 | 7.47 | | 6.41 |
| | | Leucine | |
| Ring B | | —NH$_2$ | —* |
| —NH | 7.63 | -α | 4.05 |
| -1' | 5.67 | -β's | 1.63 & |
| -2 | 5.60 | | 1.68 |
| -6 | 5.23 | -γ | 1.67 |
| | | -δ's | 0.92 & |
| | | | 0.91 |

TABLE 1-continued

Chemical Shifts for A-51568B (60° C.)

| Assignment | Chem. Shift | Assignment | Chem. Shift |
|---|---|---|---|
| Ring C | | Glucose | |
| —NH | —* | -1 | 5.33 |
| -2' | 4.81 | -2 | 5.52 |
| -1' | 5.13 | -3 | 3.48 |
| —OH | 5.83 | -4 | 3.29 |
| -2 | 7.84 | -5 | 3.16 |
| -3 | 7.16 | -6 | 3.70 & |
| -6 | 7.13 | | 3.52 |
| Ring D | | Glutamine | |
| —NH | 8.42 | -1 | 5.30 |
| -1' | 4.48 | -2 | 1.92 & |
| -2 | 6.29 | | 1.76 |
| -4 | 6.41 | (3-CH$_3$) | 1.37 |
| Ring E | | 4 | 3.16 |
| —NH | 8.48 | 5 | 4.67 |
| -1' | 4.48 | (5-CH$_3$) | 1.09 |
| -2 | 7.18 | | |
| -5 | 6.72 | | |
| -6 | 6.79 | | |

*Not assigned

The proton nuclear magnetic resonance spectrum of antibiotic A-51568B is very much like that of Vancomycin B. The chief differences noticeable by inspection are (1) the absence in the spectrum of Factor B (and also of A-51568) of the N—CH$_3$ resonance for N-methylleucine present in Vancomycin B and (2) the absence in the spectrum of Factor B of the asparagine resonances found in both Vancomycin B and A-51568 and the replacement thereof by the glutamine resonances of Factor B.

Based on proton n.m.r., mass spectral data and comparison of these data to the corresponding data of A-51568, described in U.S. application Ser. No. 450,880, an empirical formula of $C_{66}H_{75}Cl_2N_9O_{24}$ is assigned to antibiotic A-51568B.

Also a part of this invention are the pharmaceutically-acceptable, non-toxic salts of Factor B. "Pharmaceutically-acceptable" salts are salts in which the toxicity of the compound as a whole toward warmblooded animals is not increased relative to the nonsalt form. Representative and suitable salts of Factor B include those acid addition salts formed by standard reactions with both organic and inorganic acids such as sulfuric, phosphoric, hydrochloric, acetic, succinic, citric, lactic, maleic, fumaric, palmitic, cholic, pamoic, mucic, D-glutamic, d-camphoric, glutaric, glycolic, phthalic, tartaric, formic, lauric, stearic, salicyclic, methanesulfonic, benzenesulfonic, sorbic, picric, benzoic, cinnamic and the like acids; as well as those salts formed by the carboxyl group with strong bases such as sodium hydroxide, potassium hydroxide, sodium carbonate, potassium carbonate, ammonium hydroxide, diethanolamine, and like bases.

The in vitro activity of antibiotic A-51568B against a number of aerobic bacteria has been determined using a standard agar-dilution assay. The results, determined by reading the end point after 24 hours, are recorded in the following Table 2.

TABLE 2

| ACTIVITY OF A-51568B AGAINST AEROBIC BACTERIA | |
|---|---|
| Test Organism | MIC (μg/ml) |
| Staphylococcus aureus 3055 (x1.1) | 2 |
| Staphylococcus aureus V41 | 2 |

TABLE 2-continued

| ACTIVITY OF A-51568B AGAINST AEROBIC BACTERIA | |
|---|---|
| Test Organism | MIC (μg/ml) |
| Staphylococcus aureus X400 | 2 |
| Staphylococcus aureus S13E | 2 |
| Staphylococcus epidermidis EPI1 | 2 |
| Staphylococcus epidermidis 222 | 2 |
| Streptococcus pyogenes C203 | 0.5 |
| Streptococcus pneumoniae Park I | 0.6 |
| Streptococcus sp. Group D X66 | 1 |
| Streptococcus sp. Group D 2041 | 2 |
| Haemophilus influenzae (sensitive) C.L. | 128 |
| Haemophilus influenzae (resistant) 76 | 64 |
| Escherichia coli N10 | >128 |
| Escherichia coli EC14 | >128 |
| Escherichia coli TEM | >128 |
| Klebsiella pneumoniae X26 | >128 |
| Klebsiella pneumoniae KAE | >128 |
| Klebsiella pneumoniae X6B | >128 |

Factor B has been tested and found to be active against a number of anaerobic bacteria, as recorded in the following Table 3. The MIC values were determined by the agar-dilution method.

TABLE 3

| ACTIVITY OF A-51568B AGAINST ANAEROBIC BACTERIA | |
|---|---|
| Test Organism | MIC (μg/ml) |
| Clostridium difficile 2994 | 1 |
| Clostridium perfringens 81 | 1 |
| Clostridium septicum 1128 | 1 |
| Eubacterium aerofaciens 1235 | 1 |
| Peptococcus asaccharolyticus 1302 | 1 |
| Peptococcus prevoti 1281 | 4 |
| Peptostreptococcus anaerobius 1428 | 2 |
| Peptostreptococcus intermedius 1264 | 1 |
| Propionibacterium acnes 79 | 2 |
| Bacteroides fragilis 111 | 32 |
| Bacteroides fragilis 1877 | 16 |
| Bacteroides fragilis 1936B | 32 |
| Bacteroides thetaiotaomicron 1438 | 32 |
| Bacteroides melaninogenicus 1856/28 | >128 |
| Bacteroides melaninogenicus 2736 | >128 |
| Bacteroides vulgatis 1211 | 4 |
| Bacteroides corrodens 1874 | 32 |
| Fusobacterium symbiosum 1470 | 32 |
| Fusobacterium necrophorum 6054A | 128 |

Factor B has shown in vivo antimicrobial activity against experimental bacterial infections. When two doses of test compound were administered subcutaneously to mice in illustrative infections, the activity observed is measured as an ED$_{50}$ (effective dose in mg/kg to protect fifty percent of the test animals: See Warren Wick et al., *J. Bacteriol.* 81, 233–235 (1961)). The ED$_{50}$ values (expressed in units of mg/kg×2) observed for Factor B are as follows:

S. aureus 3055: 2.5
S. pyogenes C203: 7.94
S. pneumoniae Park I: 2.5

In one of its aspects this invention provides a method for treating infections in man or animals which comprises administering to said man or animal a non-toxic antibiotic-effective dose of between about 25 mg and about 2,000 mg of Factor B or a pharmaceutically-acceptable, non-toxic salt of the antibiotic.

In the treatment of infections in man, Factor B is administered by the parenteral route, e.g., by i.m. injection, or i.v. infusion. For injection, the antibiotic, or a pharmaceutically-acceptable salt thereof, in a suitable diluent at the desired concentration is administered. Suitable diluents include Water-for-Injection, 0.9% saline, 5% dextrose, Ringer's solution, or other commonly employed diluents. For administration by i.v. infusion, the antibiotic or salts thereof can be made up in a physiological fluid or dilute nutrient at a suitable concentration; for example, at a concentration between about 5% and about 10%, and slowly infused with the fluid. Alternatively, the antibiotics may be administered by the "piggy-back" method.

The antibiotic, or the pharmaceutically-acceptable, non-toxic salts thereof can be made up in dosage unit formulations in hermetically sealed vials, sterile rubber-stoppered vials, or in plastic pouches. Such unit dosage forms can contain excipients such as antioxidants, solubilizing agents, dispersing agents, buffers, and the like. One such dosage unit formulation comprises 100 mg of A-51568B antibiotic, or a pharmaceutically-acceptable, non-toxic salt thereof, in a rubber (butyl rubber) stoppered vial. Another dosage unit formulation comprises 250 mg of antibiotic A-51568B, or a salt thereof, in a sterile, sealed vial. For i.v. infusion, a dosage unit formulation of this invention comprises 5 g of Factor B or a pharmaceutically-acceptable, non-toxic salt thereof, in a plastic pouch.

When antibiotic Factor B is used as an antibacterial agent, it may be administered either orally or parenterally. As will be appreciated by those skilled in the art, the Factor B antibiotic is commonly administered together with a pharmaceutically-acceptable carrier or diluent. The dosage of the Factor B antibiotic will depend upon a variety of considerations, such as the nature and severity of the particular infection to be treated. Those skilled in the art will recognize that appropriate dosage ranges and/or dosage units for administration may be determined by considering the MIC and $ED_{50}$ values herein provided, together with factors such as the patient or host, and the infecting organism.

The A-51568B antibiotic is useful inter alia for suppressing the growth of Staphylococcus, Streptococcus, and *Propionibacterium acnes* organisms, and the antibiotic could therefore be used, for example, in the treatment of acne. Factor B in purified states can be formulated in pharmaceutically-acceptable diluents such as isopropyl alcohol for application to the skin. Such solutions can be made up with antibiotic concentrations of from about 1 to about 15 percent weight per volume. Alternatively, the antibiotic can be made up into creams or lotions for application to the skin.

Factor B is also useful for suppressing the growth of *Clostridium difficile* organisms, which cause pseudomembranous colitis in the intestine. Factor B could therefore be used in the treatment of pseudomembranous colitis by the oral administration of an effective dose of either the antibiotic or a pharmaceutically-acceptable, non-toxic salt thereof, prepared in a pharmaceutically-acceptable dosage form. For such use the antibiotic can be administered in gelatin capsules or in liquid suspension.

The antibiotics A-51568 and B are co-produced by culturing the microorganism *Nocardia orientalis* NRRL 15232, or an A-51568 and/or B-producing mutant or varient thereof, in a culture medium containing assimilable sources of carbon, nitrogen, and inorganic salts, under submerged aerobic fermentation conditions until a substantial level of antibiotic activity is produced.

A number of different media may be used in culturing *Nocardia orientalis* NRRL 15232 to produce the A-51568 and B antibiotics. For economy in production, optimal yield, and ease of product isolation, however, certain culture media are preferred. These media should contain assimilable sources of carbon, nitrogen, and inorganic salts. Suitable carbon sources include potato dextrin, glycerol, soluble starch, glucose, galactose, lactose, maltose, and refined soybean oil. Optimum levels of carbon sources are from about 2 to about 5 percent by weight. Potato dextrin and soluble starch are the more preferred carbon sources.

Preferred nitrogen sources include sodium glutamate, meat peptone, sodium nitrate, ammonium nitrate, ammonium sulfate, soybean grits, and yeast. Meat peptone (e.g., Bacto-peptone (Difco Laboratories)) is the more preferred nitrogen source.

Essential trace elements necessary for the growth and development of the organism may occur as impurities in other constituents of the media in amounts sufficient to meet the growth and biosynthetic requirements of the organism. However, it may be beneficial to incorporate in the culture media additional soluble nutrient inorganic salts capable of yielding sodium, potassium, magnesium, calcium, ammonium, chloride, carbonate, phosphate, sulfate, nitrate and like ions.

To increase production of the antibiotic mixture, various biosynthetic precursors can be added to the fermentation medium. For example, p-hydroxyphenylglycine can be added to the medium at the level of $5 \times 10^{-3}$M. Such addition was found in one experiment to increase productivity by 64%. Similar, but less spectacular increases in yield were observed by the addition of tyrosine (14%), p-hydroxyphenylglyoxylic acid (27%) and L-leucine (18%) at the same level as p-hydroxyphenylglycine. The addition of shikimic acid had no effect on the yield of the complex, while the addition of L-asparagine and L-glutamine had no significant effect on the yield.

Productivity of the antibiotic is also affected by phosphate levels. Enrichment of phosphate by as little as $3 \times 10^{-4}$M (0.05 mg/ml) was found in one experiment to depress yields by 20%.

It may be necessary to add small amounts (i.e., 0.2 ml/L) of an antifoam agent such as propyleneglycol to large-scale fermentation media if foaming becomes a problem.

The A-51568 and B-producing organism can be grown over a broad temperature range of from about 25° to about 37° C. Optimum production of the Factor B antibiotic appears to occur at a temperature of about 32° to 34° C.

Although small quantities of the A-51568 and Factor B antibiotics may be obtained by shake-flask culture, submerged aerobic fermentation in tanks is preferred for producing substantial quantities of the antibiotics. For tank fermentation, it is preferable to use a vegetative inoculum. The vegetative inoculum is prepared by inoculating a small volume of culture medium with the spore form, or mycelial fragments, to obtain a fresh, actively growing culture of the organism. The vegetative inoculum is then transferred to a larger tank where, after a suitable incubation time, the A-51568 and A-51568B antibiotics are produced in optimal yield.

An alternate method of providing inoculum for the vegetative medium consists of substituting a lyophilized pellet for the aqueous spore suspension. Lyophilized pellets are prepared in a manner known in the art. Preparation of the spore suspension for lyophilization is similar to the preparation of the aqueous spore suspension, except that sterile calf serum is substituted for sterile distilled water.

As is customary in aerobic submerged culture processes, sterile air is dispersed through the culture medium. For efficient growth of the organism, the volume of air used in tank production is in the range of from about 0.1 to about 0.25 volumes of air per volume of culture medium per minute (v/v/m), with from about 100 to about 300 RPM agitation. An optimum rate in a 165-liter vessel containing 110 liters of fermentation medium is about 0.125 v/v/m, with agitation provided by impellers rotating at about 200 RPM.

The level of antibiotic activity in the fermentation medium is determined by the following assay. A whole broth sample is centrifuged for about 15 minutes at $1000 \times g$, and the centrate removed for assay. The antibiotic activity is present in the supernatant. The assay is done microbiologically by an agar well plate test employing *Micrococcus luteus* ATCC 9341.

Production of the A-51568 and B antibiotics also can be monitored during the fermentation by either agar diffusion using *Bacillus subtilis* ATCC 6633, or a turbidimetric method using *Staphylococcus aureus* ATCC 9114.

Antibiotic activity is generally present after about 24 hours and remains present for at least 168 hours during the fermentation period. Peak antibiotic production occurs at from about 90 hours to about 114 hours fermentation time.

Factor B is then ultimately separated from A-51568 by chromatography of the filtered fermentation broth. Most of the antibiotic activity is found in the broth, while minor amounts of antibiotic activity may be associated with the mycelia. The A-51568 and B antibiotics are most readily separated from the fermentation mixture by removal of the mycelia, i.e., the biomass, by filtration. The antibiotics are then isolated from the filtered fermentation broth, preferably by column chromatography over a suitable adsorbent using an appropriate eluting agent.

Suitable adsorbents include carbon, anion and cation exchange resins, polyamide, carboxymethylcelluloses, highly porous copolymers of styrene and divinylbenzene such as Diaion HP-20, the Amberlite XAD resins, the Ionac resins, hydrophilic, insoluble, molecularsieve chromatographic media made by cross-linking dextran such as the Duolite resins, and also TSK Gels. The Diaion resins are a product of Mitsubishi Chemical Industries, Limited, Tokyo, Japan. The Amberlite XAD resins are produced by Rohm and Haas, Philadelphia, Pa. Ionac resins are available from Ionac Chemical Co., a division of Sybron Corporation, Birmingham, N.J. The Duolite resins are products of Diamond Shamrock, Redwood City, Calif. Sephadex resins are manufactured by Pharmacia Fine Chemicals AB, Uppsala, Sweden. The TSK Gels are available from E. Merck, Darmstadt, Germany, and from Bio-Rad, 2200 Wright Ave., Richmond, Calif., 94804.

In order to illustrate more fully the operation of this invention, the following Examples are provided.

In the following Examples 2, 3, and 4 the antibiotic activity of each of the collected fractions is tested using an *M. luteus* disc plate assay.

The relative amount of antibiotic activity in each fraction of these Examples is estimated by a bioassay wherein the activity of various dilutions of the fraction are compared to various dilutions of vancomycin on a disc plate assay using *M. luteus* as the test organism. The fractions are diluted and the vancomycin is dissolved in pH 6 buffer then diluted. A standard vancomycin solution is also run with each dilution. It is assumed that A-51568 and A-51568B have the same MIC against the test organisms as does vancomycin. Thus, when the zone of inhibition sizes between the fraction dilution and the vancomycin dilution are approximately the same, the amount of A-51568 and A-51568B present in the fraction can be calculated from the known concentration of vancomycin.

Finally, in Examples 2, 3 and 4 the degree of separation of A-51568 and A-51568B from other components and ultimately from each other is monitored by the use of high performance liquid chromatography (HPLC). The HPLC system used to monitor the progress of the other chromatography steps (Examples 2 and 3) is then used to separate A-51568 and A-51568B (Example 4).

Specifically, the HPLC system consists of an $8 \times 150$ mm Waters Associates Nova Pac RCM reversed phase column using an eluant flow rate of approximately 2 ml/minute at 900 p.s.i. The u.v. detector is set at 230 nm. The eluant is composed of two solvent solutions, solution A being an aqueous solution of 2% methanol, 1% tetrahydrofuran, 0.5% triethylamine (buffer) with the pH of the solution adjusted to 3.2 by the addition of phosphoric acid. Solution B is an aqueous solution of 40% methanol, 1% tetrahydrofuran, 0.5% triethylamine (buffer) with the pH of the solution was adjusted to 3.2 by the addition of phosphoric acid.

The elution with these two solutions begins with 100% solution A for 15 minutes, followed by a gradual change over a 15 minute interval to 1:1 solution A:solution B. This ratio is held for 5 minutes. The ratio is then changed over a 15 minute interval to 100% solution B, and the elution is carried on for 5 more minutes with pure solution B.

EXAMPLE 1

Preparation of First Stage Inoculum

The following medium was prepared for use in the agar slant culture of *Nocardia orientalis* NRRL 15232:

| Ingredient | Amount (g/L) |
| --- | --- |
| Precooked oatmeal | 60.0 |
| Yeast | 2.5 |
| $K_2HPO_4$ | 1.0 |
| Czapek's mineral stock | 5.0 ml/L |
| Agar | 25.0 |
| Deionized water | q.s. to 1.0 liter |

Czapek's mineral stock was prepared from the following ingredients:

| Ingredient | Amount (g/100 ml) |
| --- | --- |
| KCl | 10.0 |
| $MgSO_4.7H_2O$ | 10.0 |
| $FeSO_4.7H_2O$ | 0.2 |
| Deionized water | q.s. to 100 ml. |

Pre-sterilization pH=6.2. Adjusted to pH 7.3 with aqueous sodium hydroxide solution. Post-sterilization pH=6.7.

Spores of *Nocardia orientalis* NRRL 15232 were inoculated on an agar slant made up of the above-identified ingredients, and the inoculated slant was incubated for seven days at 30° C. The mature slant culture was then covered with sterile distilled water and scraped with a sterile tool to loosen the spores and the mycelia. One milliliter of the resulting spore suspension was used to inoculate 50 ml of vegetative medium having the following composition:

| Ingredient | Amount (g/L) |
| --- | --- |
| Glucose | 15.0 |
| Potato Dextrin | 20.0 |
| Soybean grits | 15.0 |
| Corn Steep Liquor | 10.0 |
| Yeast Extract | 1.0 |
| $CaCO_3$ | 2.0 |
| Tap Water | q.s. to 1.0 liter |

The medium had a pH of 5.5, which was adjusted to pH 6.5 with 5N sodium hydroxide solution before sterilization. Post-sterilization pH was 6.6.

The vegetative inoculum was incubated in a 250-ml wide-mouth Erlenmeyer flask at 30° C. for about 46 hours on a shaker rotating through an arc two inches in diameter at 250 RPM. This incubated medium was used to inoculate second stage flasks for the production of a larger volume of mycelia.

Specifically, one 10 ml portion per flask of the above 250 ml flask inoculum was used to inoculate two 400 ml portions of a medium with the identical composition to the above vegetative medium. These two 400 ml portions were each incubated in 2000 ml widemouth Erlenmeyer flasks at 30° C. for about 51 hours on a shaker rotating through an arc two inches in diameter at 250 RPM.

Fermentation of A51568.1

One hundred ten liters of a production medium was inoculated with approximately 0.8% (800 ml) obtained from combined volumes of the two second-stage incubated vegetative media from above. The production medium had the following composition:

| Ingredient | Amount (g/L) |
| --- | --- |
| SAG 471 (UNION CARBIDE) | 0.2 |
| Polypropyleneglycol (2000) | 0.1 |
| Potato dextrin | 30.0 |
| Blackstrap molasses | 20.0 |
| Bacto-peptone (Difco Labs.) | 7.0 |
| L-Tyrosine | 1.0 |
| Deionized water | q.s. to 110 liters |

The pH of the medium was 5.5, and was adjusted to 7.0 with aqueous 5N sodium hydroxide. The medium was sterilized at 121° C. at 17–19 psi. for 45 minutes. After sterilization, the pH of the medium was 6.2.

The inoculated production medium was fermented in a 165-liter fermentation tank for about 114 hours at a temperature of 30° C. The fermentation medium was aerated with sterile air at a rate of 0.125 v/v/m, and was stirred with conventional agitators at about 250 RPM.

The antibiotic activity is present in the supernatant of the fermentation mixture. The presence of the antibiotic activity was checked by centrifuging a sample of the whole broth at 1000×g, and decanting the centrate for assay. The sample was diluted with pH 6.0 phosphate buffer, and assayed microbiologically in an agar-well plate test using as an assay organism *Micrococcus luteus* ATCC 9341. Two fermentations using the above conditions were carried out.

EXAMPLE 2

Isolation of Antibiotic A-51568 and A-51568B Mixture

The whole broths of the above two one-hundred-ten-liter-scale fermentations were combined (approximately 230 L, total), Hyflo-Supercel (diatomaceous earth filter aid) was added and the broth was filtered using a 36" Plate Frame Filter (Sperry). The pH of the filtrate (185 L) was adjusted 6.0–6.5 by the addition of 5N hydrochloric acid. The A-51568 factors were adsorbed onto Ionac X-236 Resin (H+) (4 L. of resion per 100 L. of filtrate) and the mixture was stirred to allow adsorption of the activity. The supernatant was discarded and the resin was washed with water (10 resin volumes, approximately 40 L.). After discarding the wash, the X-236 resin was loaded into a column which was eluted with 0.1N ammonium hydroxide (5 column volumes). Antibiotic activity of the 4-liter fractions was monitored by disc plate, bioassay and HPLC. The pH of the fractions containing the two A-51568 factors was adjusted to 7.0 by the addition of 5N hydrochloric acid then pooled and loaded onto a column of Diaion HP-20 resin (5 L. of resin, 4" I.D.×42" L.) to desalt the mixture. The loading ratio of the active fractions was equivalent to 20 g vancomycin activity/liter of resin. The amount of activity present was determined by bioassay as described above. The effluent was discarded. The resin was then eluted with an aqueous solution of 5% isopropyl alcohol and 0.1% $H_3PO_4$. Fractions of 500 ml were collected and monitored for antibiotic activity using bioassay and HPLC analysis. Active fractions were combined, concentrated, and lyophilized. The resulting impure material contained about 95% A-51568 and 5% of A-51568 factor B.

EXAMPLE 3

Purification of Antibiotics A-51568 and A-51568B

To further purify the product and to simultaneously aid the separation of A-51568 and A-51568B, the lyophile from Example 2 (14.7 g) was reconstituted with deionized water (200 ml) then loaded onto CM Sephadex C-25 ($NH_4^\oplus$ cycle, 5 l of resin) (Pharmacia Fine Chemicals AB, Uppsala, Sweden) contained on a 4" I.D.×42" length glass column. The column was eluted with a linear gradient of water to 0.25N aqueous ammonium bicarbonate. The 1-liter fractions that were collected were then neutralized by the addition of 5N hydrochloric acid and the antibiotic activity of the fractions monitored by disc plate and bioassay. Also an aliquot of each of the fractions was analyzed by HPLC. A-51568 and/or A-51568B-containing fractions were grouped into 2 pools based on the ratio of A-51568 to A-51568B contained in each fraction. Pool 1 consisted of fractions 10 and 11 which contained roughly a 1:1 ratio of A-51568 to A-51568B. Pool 2 consisted of fractions 12, 13, 14, 15 and 16 which contained predominantly A-51568. As in Example 2, the pools were desalted on HP-20 resin, using the same loading ratio based on the bioassay. Specifically, Pool 1 was loaded onto 50 ml of HP-20 resin contained in a ¼" I.D. column. Pool 2 was loaded on 500 ml of HP-20 resin contained in a 1.5" I.D.×2 ft column.

Both HP-20 columns were eluted with an aqueous solution of 5% isopropyl alcohol and 0.1% phosphoric acid. The 10 ml fractions collected from each of the columns were analyzed by bioassay and HPLC. The active fractions from each pool were lyophilized.

EXAMPLE 4

Separation of A-51568 and A-51568B

The lyophilized, desalted fractions from Pool 1 of Example 3 were chromatographed on the above HPLC system to give pure A-51568 and A-51568B.

We claim:

1. Antibiotic A-51568B, which has the structure

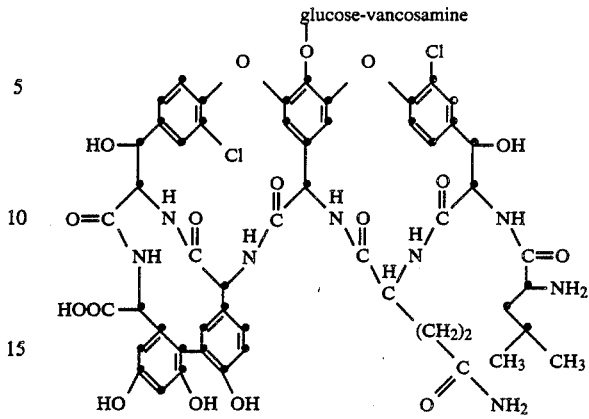

and a pharmaceutically-acceptable, non-toxic salt thereof.

2. A mixture of about 5% of antibiotic A-51568B and about 95% of antibiotic A-51568 or pharmaceutically-acceptable, non-toxic salts thereof.

3. The method for treating bacterial infections in a mammal which comprises administering to the mammal a therapeutically-effective dose of the antibiotic compound of claim 1, or a pharmaceutically-acceptable, non-toxic salt thereof.

4. A pharmaceutical composition suitable for the treatment of bacterial infections in a mammal which comprises as the active ingredient an antibiotically effective amount of the antibiotic compound of claim 1, or a pharmaceutically-acceptable, non-toxic salt thereof, and a pharmaceutically-acceptable carrier.

* * * * *